US008277371B2

(12) United States Patent
Zangen et al.

(10) Patent No.: US 8,277,371 B2
(45) Date of Patent: *Oct. 2, 2012

(54) TRANSCRANIAL MAGNETIC STIMULATION SYSTEM AND METHODS

(75) Inventors: Abraham Zangen, Jerusalem (IL); Yiftach Roth, Efrayim (IL); Pedro C. Miranda, Lisbon (PT); David Hazani, Efrayim (IL); Mark Hallet, Bethesda, MD (US)

(73) Assignees: Brainsway, Inc., Wilmington, DE (US); Yeda Research & Development Co. Ltd. at the Weizmann Institute of Science, Rehovot (IL); The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/179,525

(22) Filed: Jul. 10, 2011

(65) Prior Publication Data

US 2011/0288365 A1   Nov. 24, 2011

Related U.S. Application Data

(63) Continuation of application No. 11/153,905, filed on Jun. 16, 2005, now Pat. No. 7,976,451.

(51) Int. Cl.
  *A61N 1/00* (2006.01)
(52) U.S. Cl. .............................................. 600/13; 600/9
(58) Field of Classification Search ................ 600/9–15; 607/45
  See application file for complete search history.

(56) References Cited

U.S. PATENT DOCUMENTS

| 5,738,625 A * | 4/1998 | Gluck ............................... 600/9 |
| 2004/0078056 A1 * | 4/2004 | Zangen et al. .................... 607/2 |

\* cited by examiner

*Primary Examiner* — Charles A Marmor, II
*Assistant Examiner* — Carrie R Dorna
(74) *Attorney, Agent, or Firm* — Daniel J. Swirsky; AlphaPatent Associates Ltd.

(57) ABSTRACT

A system and methods for transcranial magnetic stimulation, the system including a helmet, a positioning portion, a stimulator and a cooling system, are disclosed. The helmet includes a coil for deep brain magnetic stimulation. The coil has a base portion, and return portions, which may include a protruding return portion and a contacting return portion. The coil is designed to minimize unintended stimulation of portions of the brain, while reducing accumulation of surface charges. The coil is stimulated at several locations and/or at different times so as to focus the electrical field on a specific deep neuronal structure.

24 Claims, 13 Drawing Sheets

TRANSCRANIAL MAGNETIC STIMULATION SYSTEM AND METHODS

CROSS-REFERENCE TO RELATED APPLICATIONS

This application is a continuation application of U.S. patent application Ser. No. 11/153,905, filed Jun. 16, 2005, U.S. Pat. No. 7,976,451 the disclosure of which is incorporated herein by reference.

FIELD OF THE INVENTION

The present invention relates to a system and methods for deep transcranial magnetic stimulation, and more particularly, to an improved system and method for stimulating specific regions of the brain while minimizing pain and side effects.

BACKGROUND OF THE INVENTION

Transcranial magnetic stimulation (TMS) is widely used as a research tool to study aspects of the human brain and has recently been used as a tool in therapeutic neuropsychiatry.

Biological tissue can be stimulated using magnetic fields produced by passing electrical currents through electrically conductive materials positioned adjacent to the tissue. The magnetic fields are intended to induce an electric field in a tissue, provided that the tissue is a conductive medium. More specifically, magnetic stimulation can cause electric conduction in brain cells, and, as a consequence, generation of action potentials.

The magnetic stimulation is delivered or generated by a coil, positioned on the patient's scalp, inducing nerve stimulation within the brain. Current magnetic stimulation techniques and coils are suitable for superficial stimulation of brain, whereas for some medical indications, deeper stimulation would be essential. As superficial stimulation does not induce effective stimulation in the prefrontal cortex (which lays 3-4 cm in depth) and other reward and mood-related brain structures such as the nucleus accumbens (ventral striatum), it may be predicted that deeper brain stimulation may be more effective for the treatment of major depression and other psychiatric and neurological disorders such as autism, post-traumatic stress disorder (PTSD), addictive behaviors including smoking, overeating and drug addiction, schizophrenia, Parkinson's disease, and others. Stimulation of deep brain regions requires a very high intensity which cannot be reached by the magnetic stimulators available today, using standard circular, figure-eight or Double Cone coils without causing undesirable side effects, such as, for example, epileptic seizures or other problems associated with over-stimulation of cortical regions.

A novel approach to TMS has been previously described in International Publication Number WO 02/32504, wherein deep brain stimulation is made possible while minimizing side effects. The device described therein includes a base and an extension portion, the base having individual windings for individual paths of current flow, and the extension portion designed so as to minimize unwanted stimulation of other regions of the brain.

SUMMARY OF THE INVENTION

According to one aspect of the present invention there is provided a coil for magnetic stimulation of a target area, wherein the coil is positionable on a body part. The coil includes a base portion, a protruding return portion, and a contacting return portion. The base portion includes at least one member for providing electrical current flow in a direction tangential to the target area, and is positioned at a first level with respect to the target area. The protruding return portion is configured for carrying returning current in a direction opposite the target area, is in electrical communication with the at least one member of the base portion, and is positioned at a second level with respect to the target area, the second level located at a distance above the first level. The contacting return portion is configured for carrying returning current in a direction opposite the target area, is in electrical communication with the at least one member of the base portion, and is positioned substantially in the first level and spaced at a distance from the target area.

According to further features in preferred embodiments of the invention described below, the at least one member can include multiple members, and in specific preferred embodiments can include 10 or 14 members. In a preferred embodiment, a portion of the multiple members is in electrical communication with the protruding return portion and a portion of the multiple members is in electrical communication with the contacting return portion. Members are positioned in a lateral-medial direction or an anterior-posterior direction, or both, and are preferably parallel to one another.

According to further features in preferred embodiments of the invention described below, the first level is on the skull, and the distance of the second level above the first level is approximately 4-10 cm and preferably around 7 cm. The distance of the contacting return portion from the target area is approximately 7-10 cm.

According to further features in preferred embodiments of the invention described below, the base portion has an arch configuration which is complementary to the body part. In a preferred embodiment, the body part is the head and the target area is a portion of the brain, wherein the base portion is configured to fit onto the head or skull of a subject. In a preferred embodiment, the portion of the brain is a deep area, and is at least 3 cm deep.

According to another aspect of the present invention there is provided a system for transcranial magnetic stimulation. The system includes a helmet for placement on a head of a subject, a positioning portion, a stimulator and a cooling system. The helmet includes at least one coil for magnetic stimulation, a rigid cover portion, and a flexible cover portion. The positioning portion includes a stand and an adjustable arm attached to the rigid cover portion of the helmet. The stimulator is in electrical communication with the coil. The cooling system includes an external unit and an internal system, wherein the internal system is in thermal proximity and approximate geometric alignment with at least a portion of the coil.

According to further features in preferred embodiments of the invention described below, the positionable portion further includes a chair and a rear head support. The system may further include an additional stimulator, in electrical communication with the coil. In preferred embodiments, the internal system is a radiator system which is separated from the coil by an insulator, such as a polyurethane resin.

According to another aspect of the present invention there is provided a method for stimulation of a deep brain region. The method includes providing a coil in accordance with preferred embodiments of the present invention described herein, placing the coil on the skull of a subject, such that a base portion and a contacting return portion are in contact with the skull and a protruding return portion is located at a distance above the skull, and activating the coil to stimulate the deep brain region.

According to further features in preferred embodiments of the invention described below, the activating includes providing electrical impulses to the coils. This can be done simultaneously, sequentially, or in a random sequence.

According to yet another aspect of the present invention there is provided a method of activating a neuronal structure. The method includes providing a coil for delivery of electrical impulses to a target area, the coil including individual members designed to carry current in predetermined directions, and activating the individual members non-simultaneously.

According to further features in preferred embodiments of the invention described below, the predetermined directions are the same direction for each of the individual members. Alternatively, the predetermined directions are a different direction for each of the individual members, and each of the predetermined directions forms a path designed to mimic a neuronal structure. In some embodiments, the activating includes sequentially activating each of the individual members, while in other embodiments, the activating includes randomly activating each of the individual members or selectively activating only some of the individual members.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1A:
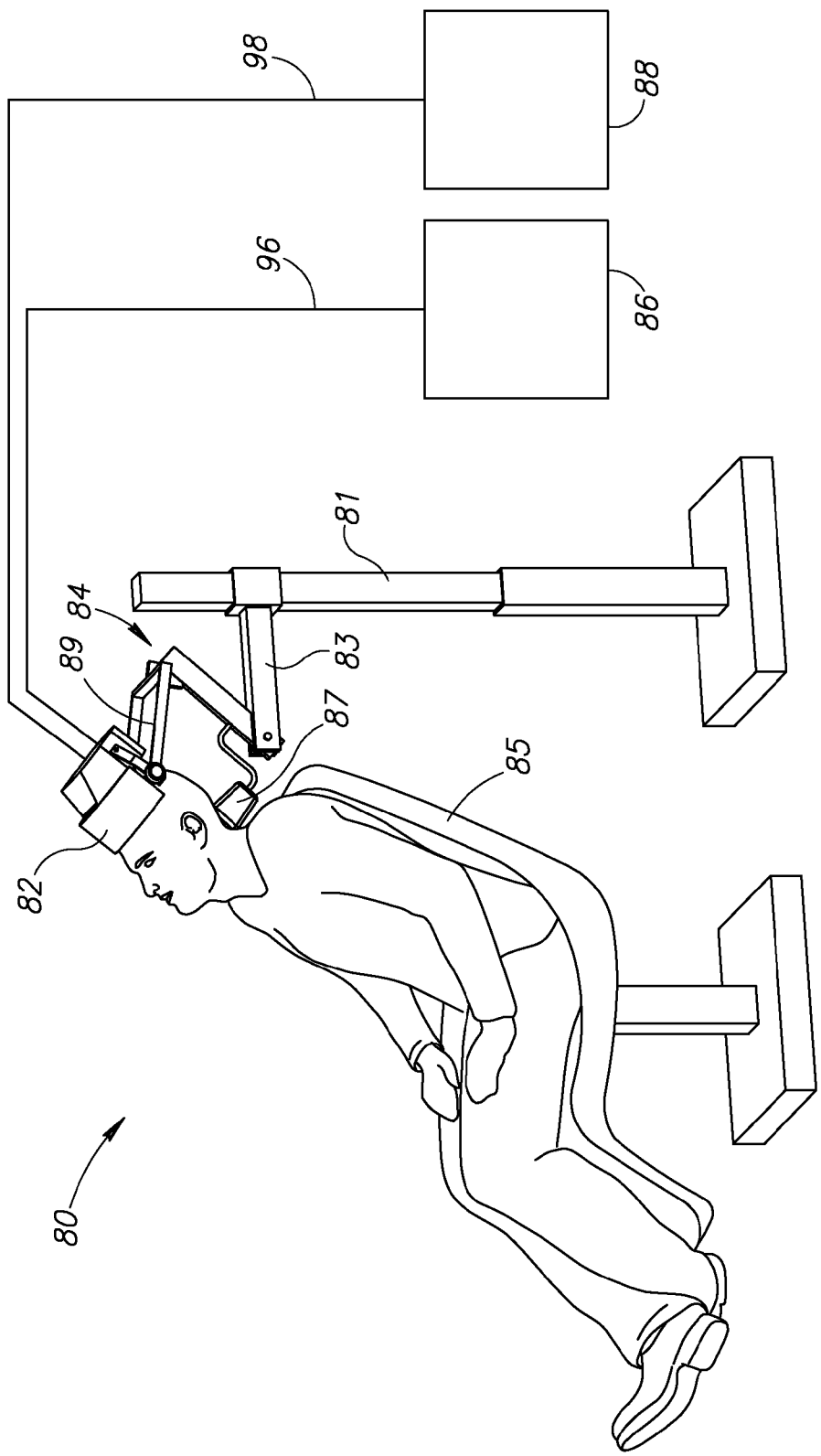
FIG. 1A is a schematic illustration of a system in accordance with a preferred embodiment of the present invention.

The present invention is of a method for stimulating deep brain regions using TMS. Specifically, the present invention can be used to stimulate deep regions of the brain while maintaining a high percentage of field intensity as compared to superficial regions.

The principles and operation of a system and methods for transcranial magnetic stimulation according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Reference is now made to FIG. 1A, which is a schematic illustration of a system 80 in accordance with a preferred embodiment of the present invention. System 80 includes a helmet 82 which holds coils for magnetic stimulation and is positionable around a head of a subject. Helmet 82 is adjustable via positioning portion 84. Positioning portion includes a stand 81 with an adjustable arm 83, a chair 85 with a rear head support 87, and an adaptor 89 between helmet 82 and adjustable arm 83. A stimulator 86 is in electrical communication with the coils of helmet 82, and is designed to provide electrical stimulation to the coils. Stimulator 86 is a commercially available neurostimulator, such as any of the various models of magnetic stimulators produced by Medtronic, Inc. of Minneapolis, Minn., USA (e.g., MagPro, MagLite Compact), or power supplies sold with various models of magnetic stimulators produced by Magstim Company US, LLC, of New York, N.Y., USA (e.g., Magstim Model 200, Magstim Model 220, Magstim Model 250, BiStim, Magstim Rapid, Magstim QuadroPulse). Stimulator 86 is used to deliver electrical stimulation to the brain, and provides a controlled output, frequency, and pulse duration, and may also include an indication of coil temperature. A cooling system 88 is also in communication with the coils of helmet 82, and is designed to maintain an ambient temperature in the coils during repetitive stimulation provided by stimulator 86. Cooling system 88 may be a system based on air cooling using a Freon system, or a thermoelectric cooler (TEC) system such as the TECs produced by Melcor Ltd, (Trenton, N.J., USA), with either open air pathways or closed, two-direction air pathways, or cooling system 88 may be a liquid cooling system. A particular example of a cooling system 88, designed specifically for use with the coils of the present invention, will be described in further detail herein below with respect to FIGS. 6-9.

Figure 1B:
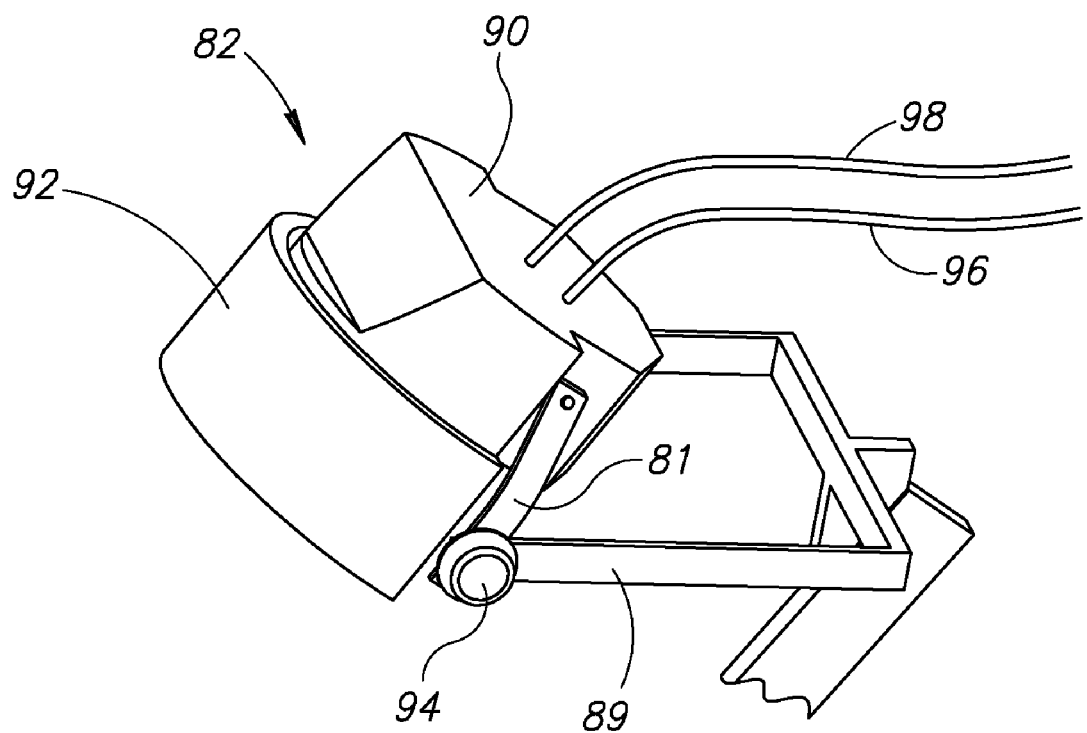
FIG. 1B is an illustration of a helmet from the system of FIG. 1A.

Reference is now made to FIG. 1B, which is a more detailed schematic illustration of helmet 82 in accordance with a preferred embodiment of the present invention. Helmet 82 includes a rigid cover 90 and a flexible cover 92. Flexible cover 92 is designed to provide flexibility over the head. An internal wall of helmet 82 is lined with a sponge for padding. In one embodiment, the liner is a 0.9 mm biocompatible sponge with one-sided glue (3M Foam Medical Tape). Adaptor 89 is attached to an upper portion of stand 81 via an adjustment screw 94. Adjustment screw 94 enables adjustment of the height or angle of helmet 82. Wires 96, 98 run from stimulator 86 and cooling system 88 to helmet 82.

Positioned within helmet 82 are coils for transcranial magnetic stimulation. Coils are designed to penetrate deep regions of the brain, while minimizing adverse side effects. The basic principles of operation of coils suitable for deep brain stimulation are as follows:

1. Proper Orientation of Stimulating Coils.

Coils must be oriented such that they will produce a considerable field in a direction tangential to the surface, which should also be the preferable direction to activate the neurons under consideration. That is, wires of the coils are directed in one or more directions, which results in a preferred activation of neuronal structures orientated in these particular directions. In some cases, there is one preferred direction along the length or width axis, and in other cases, there are two preferred directions along both the length and width axes. Thus, the placement and orientation of activating coils on the skull is important.

2. Minimization of Non-Tangential Coil Elements.

Electrical field intensity in the tissue to be stimulated and the rate of decrease of electrical field as a function of distance from the coil depend on the orientation of the coil elements relative to the tissue surface. It has been shown that coil elements which are perpendicular to the surface induce accumulation of surface charge, which leads to in cancellation of the perpendicular component of the induced field at all points within the tissue, and reduction of the electrical field in all other directions. Thus, the length of coil elements which are not tangential to the brain tissue surface should be minimized. Furthermore, the non-tangential coil elements should be as small as possible and placed as far as possible from the deep region to be activated. The combination of these two factors helps to minimize accumulation of surface charge.

3. Maximization of the Field in the Deep Region as Compared with the Field at the Cortex.

A major goal of deep TMS is to maximize deep region stimulation without causing a large electrical field at surface areas of the brain. If the electrical field at the surface areas is too large, it can cause pain, epileptic seizures, or other complications. Thus, it is important to try to maximize deep region stimulation without causing a large electrical field to accumulate at surface areas. This can be accomplished by summation of electrical impulses, a concept which will be described further hereinbelow. In addition the coil elements leading currents in a direction opposite to the preferred direction (the return paths), should be located far from the desired brain region.

For purposes of better understanding the present invention, as illustrated in FIGS. 4-10 of the drawings, reference is first made to the construction and operation of prior art coils as illustrated in FIGS. 2A, 2B, 3A and 3B. The coils are shown in two different, which have been previously disclosed in International Publication Number WO 02/32504, entitled, "Coil for magnetic stimulation and methods for using the same," incorporated by reference herein in its entirety.

Figure 2A:
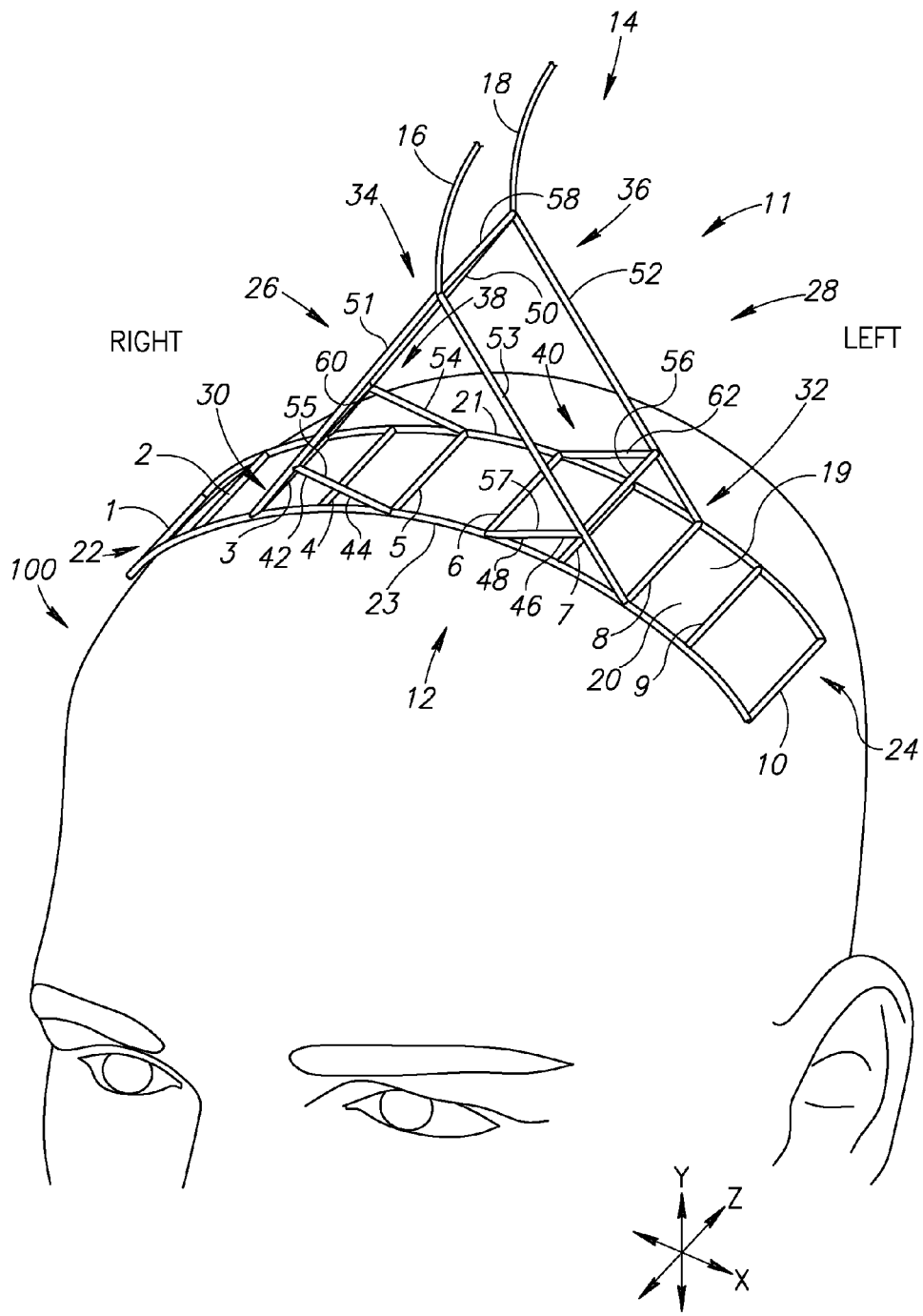
FIG. 2A is an illustration of a prior art device including a frame and an electrically conductive coil having a base and an outwardly projecting extension portion.

Referring now to FIG. 2A, a device 11 includes a frame and an electrically conductive coil having a base 12 and an outwardly projecting extension portion 14. In some embodiments, the frame itself is the electrically conductive coil, such as a frame composed of electrically conductive material. In other embodiments, however, the frame is a flexible or malleable material, which may be configured to a desired shape for a specific application, and the electrically conductive coil comprises one or more windings of electrically conductive material associated with the frame, such as being run alongside of, mounted to, wound around, or placed inside the frame. The base 12 has a concave first side 19, which is directed toward the body part of the subject, and a second side 20 opposite first side 19. The extension portion 14 extends outwardly from this second side and away from the base.

Device 11 can be placed in various orientations around the skull. However, device 11 effectively induces electric fields within the body of a subject when the device 11 is placed with the concave side 19 of the base 12 facing the body of the subject.

The device 11 pictured in FIG. 2A has a partially toroidal or ovate base 12 with a first end 22 and a second end 24. A line extending between these two ends 22, 24 defines a length axis along the length of the base 12. The base 12 has a substantially arcuate, semi-circular or semi-ovate shape along its length axis. The base 12 also has a width axis extending perpendicular to its length axis and this width axis has a substantially arcuate, semi-circular or semi-ovate shape. Thus, the base 12 pictured in FIG. 2A comprises an arch extending along its length axis and an arch extending along its width axis. The arch configurations along both the length and width axes are complementary to the external shape of the body part with which the device is to be used. The device conforms to the side-to-side and front-to-back arch shape of a subject's skull.

As shown in FIG. 2A, the base 12 includes a pair of substantially parallel, arcuate, elongate, longitudinally-extending, laterally spaced frame members 21 and 23. Extending between and interconnecting longitudinal frame members 21 and 23 are ten elongate, arcuate, transverse frame members 1, 2, 3, 4, 5, 6, 7, 8, 9, 10. Members 1-10 are spaced apart along the lengths of longitudinal frame members 21 and 23 and are coupled at their opposite ends to, and extend generally at right angles to, longitudinal frame members 21 and 23.

The extension 14 provides a path for the flow of electricity to and from the base 12. A surface charge can interfere with and reduce the strength of the electric field produced by the coil portions in the base. Reduction in surface charge is accomplished by using a triangular, or upwardly converging, extension 14. The extension 14 comprises first and second elongated elements 26, 28. The elements have a first set of inner ends 30, 32 connected to the base 12 at positions spaced apart along the length of the axis of the base 12. The first elongated element 26 has a first inner end 30 connected to the base 12 adjacent to the first end 22 of the base 12, and the second elongated element 28 has a first inner end 32 connected to the base 12 adjacent to the second end 24 of the base 12. The remainder portions 34, 36 of these elements 26, 28 extend away from the base 12 and converge toward each other.

Figure 2B:
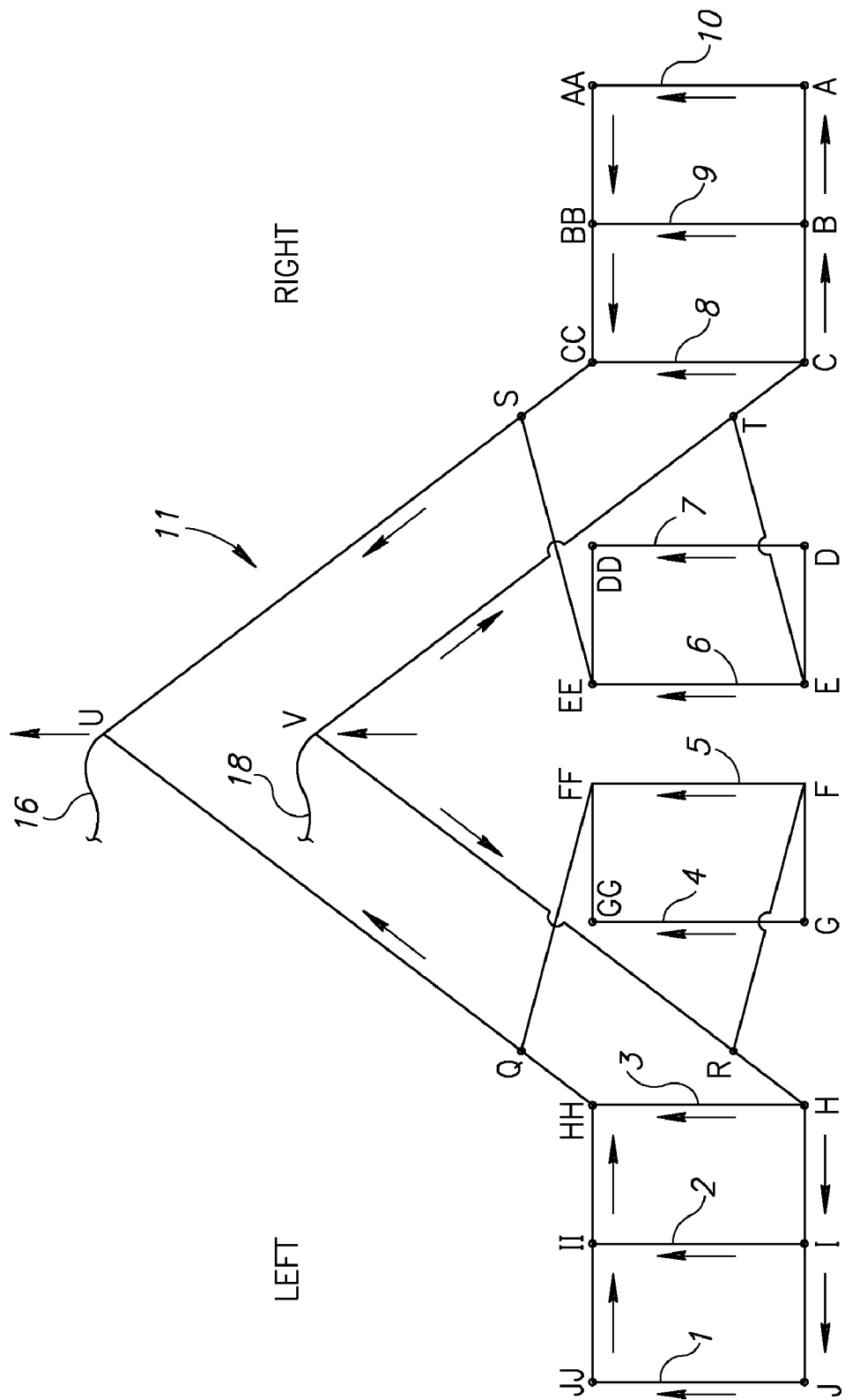
FIG. 2B is a schematic diagram illustrating conducting wires and current flow in the prior art embodiment illustrated in FIG. 2A.

FIG. 2B is a schematic diagram illustrating conducting wires and current flow in the embodiment illustrated in FIG. 2A. In FIG. 2B, points labeled A-J and AA-JJ are associated with the base, and points Q-V are associated with the extension portion. Points U and V correspond to the electrical inputs for the current produced by the power supply (not shown). Using the diagram of FIG. 2B as a guide, one can understand how a coil might be constructed for the embodiment of FIG. 2A. For example, the device 11 illustrated by FIG. 2A could comprise a coil having ten windings numbered 1-10 extending in the arch width direction of the base along the ten elongate, arcuate transverse frame members 1-10. Table 1 summarizes such a placement of windings.

TABLE 1

| Winding No. | Pathway |
| --- | --- |
| 1 | V-R-H-I-J-JJ-II-HH-Q-U |
| 2 | V-R-H-I-II-HH-Q-U |
| 3 | V-R-H-HH-Q-U |
| 4 | V-R-F-G-GG-FF-Q-U |
| 5 | V-R-F-FF-Q-U |
| 6 | V-T-E-EE-S-U |
| 7 | V-T-E-D-DD-EE-S-U |
| 8 | V-T-C-CC-S-U |
| 9 | V-T-C-B-BB-CC-S-U |
| 10 | V-T-C-B-A-AA-BB-CC-S-U |

A significant portion of the current flowing through the base flows through the transverse strips of the coil and therefore, is oriented substantially along the reference z-axis shown in FIG. 2A. The coil portions associated with the base are complementary and tangential to the surface of the subject's skull. In particular embodiments, the total length of the coil associated with the transverse frame elements 1-10 (i.e. substantially parallel to the width axis of the base) exceeds the remaining length of the coil associated with the base (i.e. the remaining length substantially parallel to the length axis of the base). In these embodiments, a majority of the current flowing through the base is oriented substantially along the referenced z-axis shown in FIG. 2A.

Figure 3A:
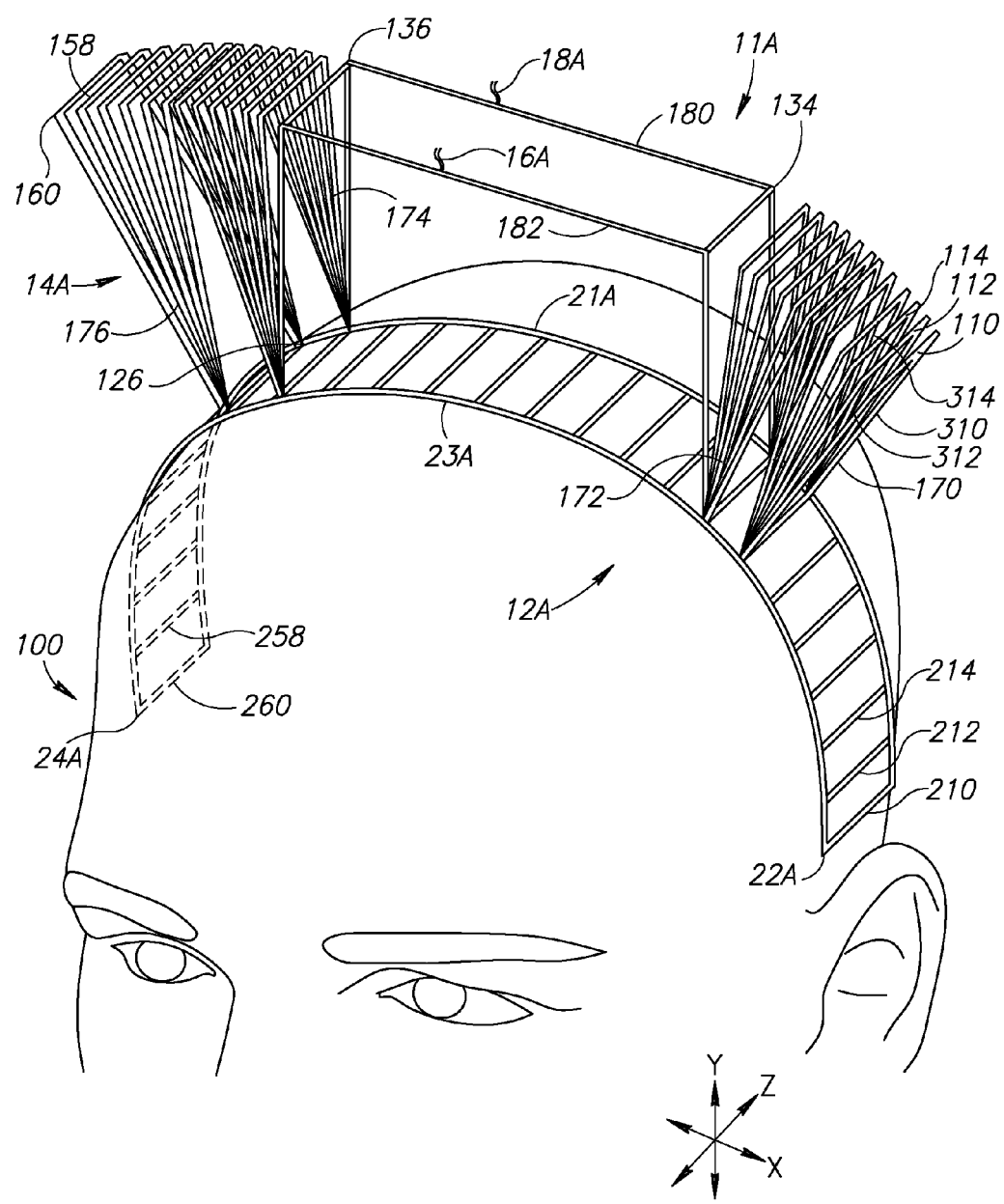
FIG. 3A is an illustration of a prior art device including a frame and an electrically conductive coil having a base and an outwardly projecting extension portion with a plurality of radially elongated extension elements.
Figure 3B:
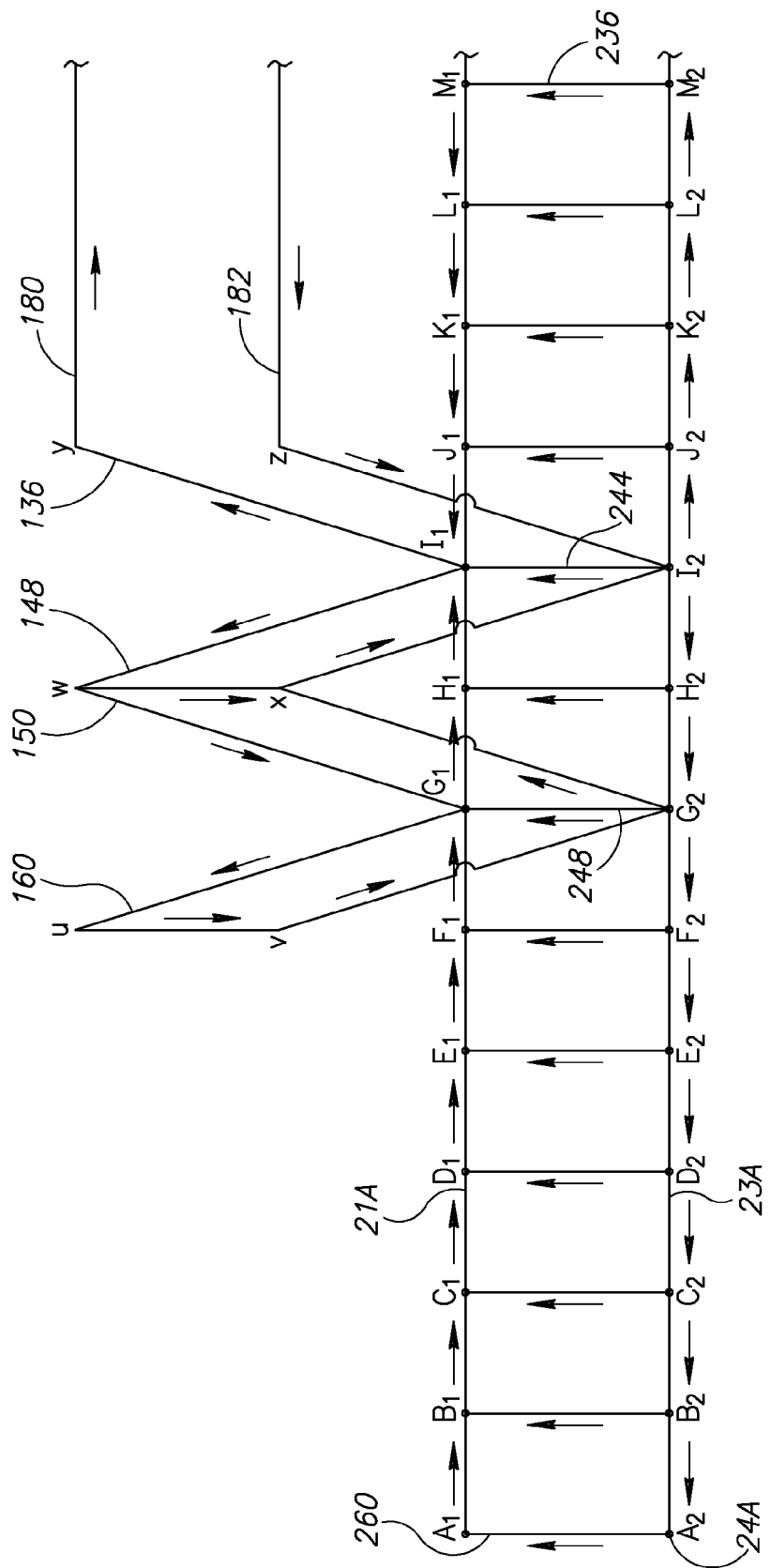
FIG. 3B is a schematic diagram illustrating conducting wires and current flow in the prior art embodiment illustrated in FIG. 3A.

An alternative embodiment of the device disclosed in International Publication Number WO 02/32504 is depicted in FIGS. 3A and 3B. A device 11A has a base 12A and an extension portion 14A, where base 12A has a first end 22A and a second end 24A, and a substantially arcuate, semi-circular or semi-ovate shape along its length and width axes. However, in this embodiment, extension 14A includes a plurality of radially elongated extension elements 110, 112, 114, . . . 158, 160, rather than a minimal number of radially elongated elements 26, 28 shown in FIG. 2A. The embodiment shown in FIG. 3A includes twenty-six radially extending elongated extension elements 110, 112, 114, . . . 158, 160, although alternative embodiments may employ a different number of such elongated extension elements. As illustrated, the radially elongated elements 110, 112, 114, . . . 158, 160 are collected into four fan-like groupings 170, 172, 174, 176, and elongated elements 134 and 136 are connected by lateral elements 180 and 182.

Similar to base 12 illustrated in FIG. 2A, base 12A illustrated in FIG. 3A includes a pair of substantially parallel, arcuate, elongate, longitudinally-extending, laterally spaced frame members 21A and 23A. Extending between and interconnecting longitudinal frame members 21A and 23A are twenty-six elongate, arcuate transverse frame members 210, 212, 214, . . . 258, 260.

The amount of surface charge, and the influence of that surface charge on the deeper tissues of the subject's body that are stimulated, depends on the overall lengths and locations of the electrical components which contain non-tangential components. In this embodiment, the overall lengths of such non-tangential elements are reduced and their distances from the deep brain regions aimed for activation are increased. In other words, the ratio of the total length of the coil extending radially from the base to the total length of the coil associated with the base is less than the corresponding ratio in the previous embodiment, shown in FIG. 2A.

FIG. 3B is a schematic illustration of current flow through the windings of the embodiment illustrated in FIG. 3A, with reference numerals correlating these windings to certain structures illustrated in FIG. 3A. FIG. 3B is not a circuit diagram in the true sense—this illustration simply shows how a coil for the device may be made from individual windings of the coil, with each individual winding comprising a circuit. For the sake of clarity, only part of the entire device is shown.

As illustrated in FIG. 3B, the direction of electrical current flow is the same in all of the twenty-six strips of the base 12A, flowing in a direction from the lateral frame member 23A to lateral frame member 21A. Generally, current to this portion of the coil arrives at Z, travels down to $I_2$, and flows through strips $J_2$-$J_1$, $K_2$-$K_1$, $L_2$-$L_1$, and $M_2$-$M_1$. Each strip ($A_2$-$A_1$, $B_2$-$B_1$, . . . $M_2$-$M_1$) has a return path through an elongated element 110, 112, 114, . . . 158, 160 of one of the fan-like groupings 170, 172, 174, 176. For example, the return path for strip $J_2$-$J_1$ may be elongated element 140 (not shown in FIG. 3B). The current flows to $I_2$ then flows through strip $H_2$-$H_1$, and to $I_1$. From here, the current flows up the extension to W, then to X (the line W-X representing the junction of two elongated elements 148 and 150), then to $G_2$, then through strips $F_2$-$F_1$, $E_2$-$E_1$, $D_2$-$D_1$, $C_2$-$C_1$, $B_2$-$B_1$, $A_2$-$A_1$, and returns to $G_2$. Each of strips $F_2$-$F_1$, $E_2$-$E_1$, $D_2$-$D_1$, $C_2$-$C_1$, $B_2$-$B_1$, $A_2$-$A_1$, has a return path through an elongated element of fan-like collection 176 composed of elongated elements 150-160. The return paths of current flow are in the opposite directions of the strips. As in the first embodiment, shown in FIG. 2A, extension portion 14A of this second embodiment places electrical currents flowing through the return paths away from the subject, to reduce their electrical effect on the body tissues of the subject.

In the two prior art embodiments of a device for magnetic stimulation described above with reference to FIGS. 2A-B and 3A-B, return paths are placed away from the subject, to reduce their electrical effect on the body tissues of the subject. However, increasing the distance from the skull requires longer non-tangential elements and causes an accumulation of surface charges, which increases the decay in electrical field with depth. These conflicting principles are balanced as much as possible, so as to minimize both unwanted electrical effects due to current flow in the return paths and unwanted accumulation of surface charges.

In the present invention, a design to further decrease the lengths of non-tangential elements (and thus minimize unwanted surface charges at the area of stimulation) is described. The embodiments described herein are particularly useful in cases where the region to be stimulated is not on a central line of the brain, such as prefrontal regions.

Figure 4:
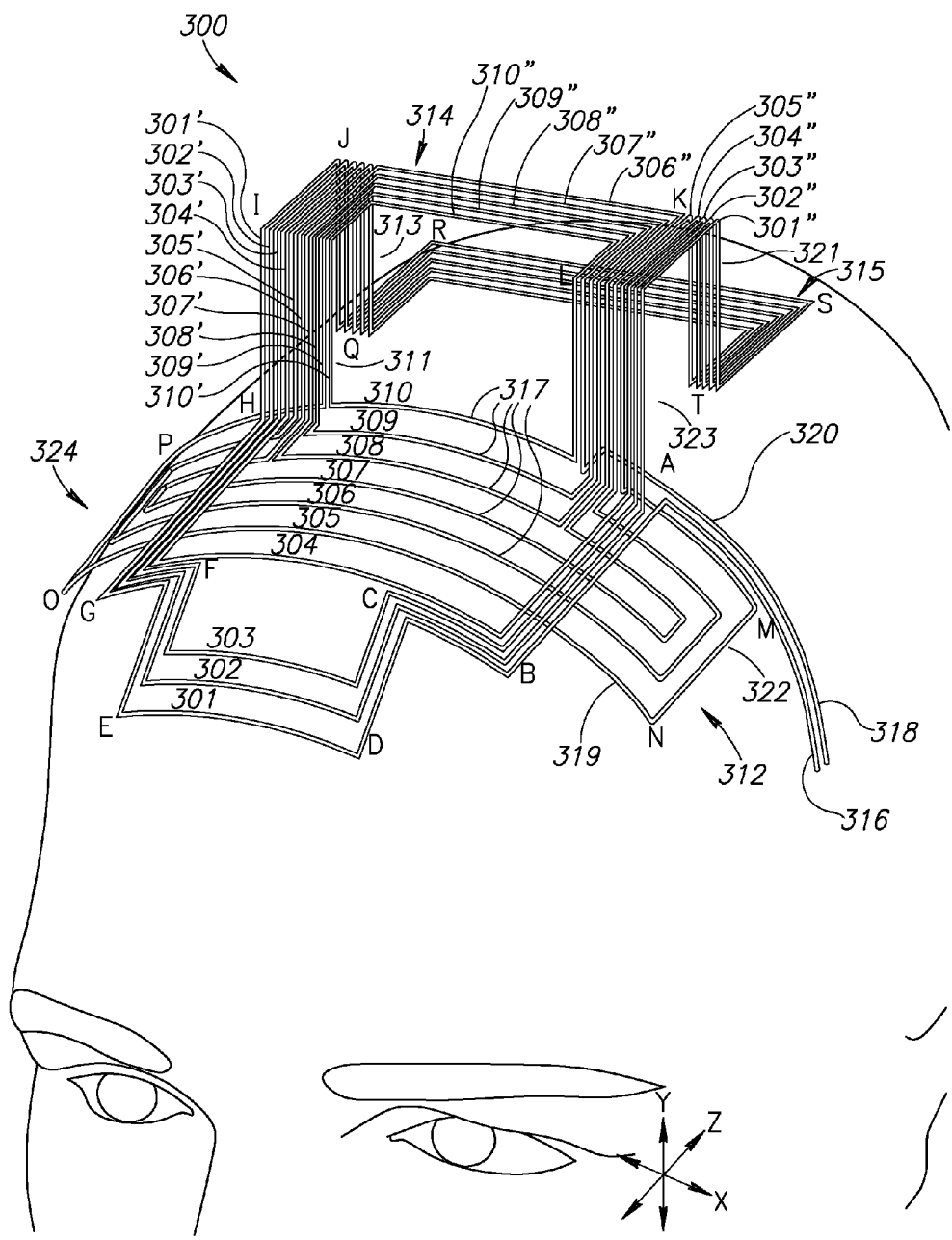
FIG. 4 is an illustration of a coil for TMS in accordance with one preferred embodiment of the present invention.

Reference is now made to FIG. 4, which is an illustration of a coil 300 for TMS in accordance with one preferred embodiment of the present invention. Coil 300 includes a base portion 312, a protruding return portion 314, and a contacting return portion 315. Base portion 312 is comprised of windings 317 of electrically conductive material. Base portion 312 has a concave first side 319, which is in direct contact with the skull and is directed toward the body part of the subject, and a second side 320 opposite first side 319. Protruding return portion 314 extends outwardly from second side 320 and away from base portion 312, and contacting return portion 315 is positioned a distance from base portion 312, but is in contact with the skull. Thus, base portion 312 can be considered to be at a first level with respect to the target area. Protruding return portion 314 is at a second level which is at a distance from the first level in the y-direction. Contacting return portion 315 is at the first level, that is, is approximately on the same plane as base portion 312, but is at a planar distance (in the x-z plane) from the target area. Windings 317 are designed to be in contact with the skull, and may either be pre-formed or malleable to accommodate the curved anatomy of the area on which it is to be placed. This design maximizes tangential stimulation, which is optimal for axonal depolarization.

The device 300 pictured in FIG. 4 has an arcuate base 312 with a first end 322 and a second end 324. A line extending between these two ends 322, 324 defines a length axis along the length of the base 312. The base 312 has a substantially arcuate, semi-circular or semi-ovate shape along its length axis. The base 312 also has a width axis extending perpendicular to its length axis and this width axis has substantially arcuate, semi-circular or semi-ovate shape. Thus, the base 312 pictured in FIG. 4 comprises an arch extending along its length axis and an arch extending along its width axis. The arch configurations along both the length and width axes are complementary to the external shape of the body part with which the device is to be used. The device conforms to the side-to-side and front-to-back arch shape of a subject's skull.

Base 312 includes windings 317, which are comprised of a series of substantially parallel members 301-310. In the embodiment depicted in FIG. 4, members 301-310 are oriented in a lateral-medial direction, making device 300 suitable for activating structures in the prefrontal cortex and fibers connecting the cingulate or prefrontal cortex with the nucleus accumbens and ventral tegmental area. These are neuronal pathways related to the control of motivation, reward and pleasure. Each of members 301-310 carries an electrical current in the lateral-medial direction (substantially parallel with the length axis of base 312), with the direction of the current being the same in each of members 301-310. Each of members 301-310 has a return path, extending through either protruding return portion 314 or through contacting return portion 315. The members 301-310 are electrically connected to a power supply, such as by electrical leads 316, 318. In a preferred embodiment, each of members 301-310 is 14-22 cm in length. In one embodiment, there is a separation of 0.5-1.5 cm between each of members 301-310. In a preferred embodiment, there is a separation of 0.8 cm between each of members 301-310. The return paths 306"-310" of members 306-310 are situated above the head at a distance therefrom as delineated by segments H-I. In one embodiment, the distance from the head to the return paths 306"-310" of members 306-310 is between 4-10 cm. In a preferred embodiment, the distance from the head to the return paths 306"-310" of members 306-310 is approximately 7 cm.

Coil 300 may be composed of any electrically conductive material, such as metal. Particular embodiments have coils comprising wire made of copper, aluminum, or other electrically conductive material. In a preferred embodiment, the coil is made of a double 14 AWG insulated copper wire having a total length of 800 cm and winded into windings 317, connected in series. In another embodiment the coil is made from a multiline wire composed of 40-60 lines of 3 mm cross section. In a preferred embodiment, coil elements are coated by a polyurethane resin type Resinex 4 (Hamchaber Vehamkasher Ltd., Israel), for additional electrical insulation. In alternative embodiments, coil elements are coated by other insulating materials, such as PVC, or are sandwiched between layers of insulating materials. It should be readily apparent that the embodiments disclosed herein are examples only and should not be regarded as limiting. The windings 317 are connected to an appropriate cable and connector, which is then connected to a stimulator. The stimulator may be any appropriate commercially available power supply, such as the power supplies available for use with other magnetic coils. In preferred embodiments, the stimulator is one of various models of magnetic stimulators produced by Medtronic, Inc. of Minneapolis, Minn., USA (e.g., MagPro, MagLite Compact), or power supplies sold with various models of magnetic stimulators produced by Magstim Company US, LLC, of New York, N.Y., USA (e.g., Magstim Model 200, Magstim Model 220, Magstim Model 250, BiStim, Magstim Rapid, Magstim QuadroPulse).

A power supply or stimulator (not shown) supplies current through lead 316 into one of members 301-310. The stimulating current pulses flow substantially in the lateral-medial direction. Current then ascends through an ascending portion 311 extending upwards from base portion 312. At this point, current can take one of two paths—either through protruding return portion 314 or through contacting return portion 315. If current runs through protruding return portion 314, it runs from ascending portion 311, through protruding return portion (which runs substantially parallel to members of base portion 312), and back down to the level of the skull at a descending portion 323. From there, current returns through lead 318 back into the power supply. If current runs through contacting return portion 315, it runs from ascending portion 311, to a descending connector 313, through contacting return portion 315 (which runs substantially parallel to members of base portion 312 and is positioned directly on the skull, but at a distance from members 301-310 of base portion 312), to an ascending connector 321, and back down to the level of the skull at descending portion 323. From there, current returns through lead 318 back into the power supply. In a preferred embodiment, half of the members run through protruding return portion 315 and half of them run through contacting return portion 314. However, the invention is not limited to this proportion, and any proportion of protruding return paths and contacting return paths is possible, so long as each return path receives current from at least one of the members. Current may be supplied simultaneously to all members, or alternatively, may be supplied sequentially, in a random order, or selectively. In another embodiment, current is supplied to member 301, and runs through a loop including each of the additional members 301-310. It should also be readily apparent that although the invention has been shown with reference to ten members, the invention is not in any way limited to this number, and any suitable number of members may be used. In additional embodiments, a single member may have a return path through both protruding return portion 314 and contacting return portion 315.

In the preferred embodiment depicted in FIG. 4, current from each of members 301-310 runs through ascending portion 311 via pathways 301'-310'. At the top of ascending portion 311, current from members 301-305 runs through contacting return portion 315 via pathways 301"-305" while current from members 306-310 runs through protruding return portion 314 via pathways 306"-310". Specifically, members 301-303 traverse the path A-B-C-D-E-F-G-H-I-J-Q-R-S-T-K-L-A. Member 304 traverses the path A-B-G-H-I-J-Q-R-S-T-K-L-A. Member 305 traverses the path A-M-N-B-G-O-P-H-I-J-Q-R-S-T-K-L-A. Members 306-307 traverse the path A-M-N-B-G-O-P-H-I-J-K-L-A. Members 308-309 traverse the path A-B-G-H-I-J-K-L-A. Member 310 traverses the path A-H-I-J-K-L-A. It should be readily apparent that other combinations and pathways are possible, and are within the scope of the present invention.

Protruding return portion 314 is spaced a distance from the skull, as described above. By placing the return path at a distance from the skull, electrical stimulation of unwanted portions of the brain is minimized. However, surface charge accumulation at the surface of the brain is increased. As such, some of the return paths are placed on the skull itself, so as to reduce surface charge accumulation. However, these return paths are placed a distance from the site to be stimulated within the brain so as to avoid conflicting signals in the area of stimulation. In a preferred embodiment, the distance from the members to the contacting return paths is at least 5 cm. In some embodiments, the distance from the members to the contacting return paths is in the range of 7-20 cm. In a preferred embodiment, the distance is approximately 10 cm. Thus, a balance is maintained between the need for reducing surface charge and the conflicting need to avoid electrical stimulation of unwanted portions of the brain.

Figure 5:
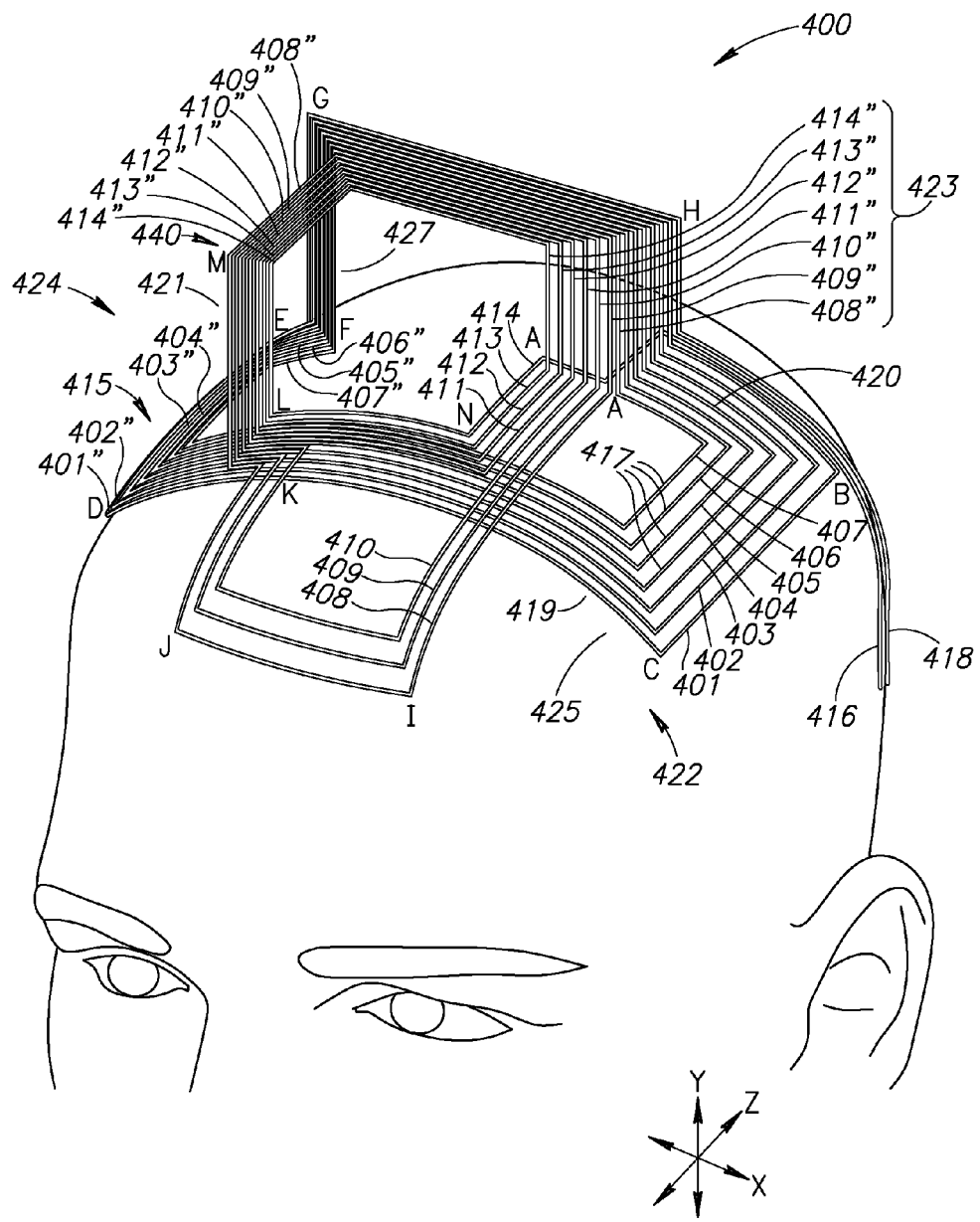
FIG. 5 is an illustration of a coil for TMS in accordance with another preferred embodiment of the present invention.

Reference is now made to FIG. 5, which is an illustration of a coil 400 for TMS in accordance with another preferred embodiment of the present invention. In this embodiment, members 401-414 are oriented in an anterior-posterior direction, for activation of structures in the prefrontal cortex and fibers connecting the cingulate or prefrontal cortex with the nucleus accumbens and ventral tegmental area, with preference for the left hemisphere These are neuronal pathways related to the control of motivation, reward and pleasure. Coil 400 includes a base portion 425, a protruding return portion 440, and a contacting return portion 415. Base portion 425 is comprised of windings 417 of electrically conductive material. Base portion 425 has a concave first, or inner side 419, which is in direct contact with the skull and is directed toward the body part of the subject, and a second, or outer side 420 opposite first side 419. Protruding return portion 440 extends outwardly from second side 420 and away from base portion 425, and contacting return portion 415 is positioned a distance from base portion 425, but is in contact with the skull. Thus, base portion 425 can be considered to be at a first level with respect to the target area. Protruding return portion 440 is at a second level which is at a distance from the first level in the y-direction. Contacting return portion 415 is at the first level, that is, is approximately on the same plane as base portion 425, but is at a planar distance (in the x-z plane) from the target area. Windings 417 are designed to be in contact with the skull, and may either be pre-formed or malleable to accommodate the curved anatomy of the area on which it is to be placed. This design maximizes tangential stimulation, which is optimal for axonal depolarization.

The device 400 pictured in FIG. 5 has an arcuate base 425 with a first end 422 and a second end 424. A line extending between these two ends 422, 424 defines a length axis along the length of the base 425. The base 425 has a substantially arcuate, semi-circular or semi-ovate shape along its length axis. The base 425 also has a width axis extending perpendicular to its length axis and this width axis has substantially arcuate, semi-circular or semi-ovate shape. Thus, the base 425 pictured in FIG. 5 comprises an arch extending along its length axis and an arch extending along its width axis. The arch configurations along both the length and width axes are complementary to the external shape of the body part with which the device is to be used. The device conforms to the side-to-side and front-to-back arch shape of a subject's skull.

Base 425 includes windings 417, which are comprised of a series of substantially parallel members 401-414. In the embodiment depicted in FIG. 5, members 401-414 are oriented in an anterior-posterior direction, making device 400 suitable for activating structures in the prefrontal cortex. Each of members 401-414 carries an electrical current in the anterior-posterior direction (substantially perpendicular with the length axis of base 425), with the direction of the current being the same in each of members 401-414. Each of members 401-414 has a return path, extending through either protruding return portion 440 or through contacting return portion 415. The members 401-414 are electrically connected to a power supply, such as by electrical leads 416, 418. In a preferred embodiment, each of members 401-414 has a length of 7-12 cm. The 14 members 401-414 are distributed above the prefrontal cortex of the left hemisphere. In one embodiment, there is a separation of 0.5-1.5 cm between each of members 401-414. In a preferred embodiment, there is a separation of 1 cm between each of members 401-414. Three members 408-410 are elongated towards the forehead, and their continuations pass in the left-right direction along the orbitofrontal cortex to provide additional effects in that region, as delineated by segments I-J. Return paths 401"-407" of members 401-407 are attached to the head in the right hemisphere, as delineated by segments D-E. In one embodiment, each of the return paths 401"-407" is separated from one another by approximately 0.5-1.2 cm. In a preferred embodiment, each of the return paths 401"-407" is separated from one another by approximately 0.8 cm. The return paths 408"-414" of members 408-414 are situated above the head at a distance therefrom as delineated by segments M-G. In one embodiment, each of the return paths 408"-414" is separated from one another by approximately 0.1-0.7 cm. In a preferred embodiment, each of the return paths 401"-407" is separated from one another by approximately 0.3 cm. In one embodiment, the distance from the head to the return paths 408"-414" of members 408-414 is between 4-10 cm. In a preferred embodiment, the distance from the head to the return paths 408"-414" of members 408-414 is approximately 7 cm.

Coil 400 may be composed of any electrically conductive material, such as metal. Particular embodiments have coils comprising wire made of copper, aluminum, or other electrically conductive material. In a preferred embodiment, the coil is made of a double 14 AWG insulated copper wire having a total length of 750 cm and winded into windings 417, connected in series. In a preferred embodiment, coil elements are coated by a polyurethane resin type Resinex 4 (Hamchaber Vehamkasher Ltd., Israel), for additional electrical insulation. In alternative embodiments, coil elements are coated by other insulating materials, such as PVC, or are sandwiched between layers of insulating materials. It should be readily apparent that the embodiments disclosed herein are examples only and should not be regarded as limiting. The windings 417 are connected to an appropriate cable and connector, which is then connected to a stimulator. The stimulator may be any appropriate commercially available power supply, such as the power supplies available for use with other magnetic coils. In preferred embodiments, the stimulator is one of various models of magnetic stimulators produced by Medtronic, Inc. of Minneapolis, Minn., USA (e.g., MagPro, MagLite Compact), or power supplies sold with various models of magnetic stimulators produced by Magstim Company US, LLC, of New York, N.Y., USA (e.g., Magstim Model 200, Magstim Model 220, Magstim Model 250, BiStim, Magstim Rapid, Magstim QuadroPulse).

The stimulator or power supply (not shown) supplies current through lead 416 into one of members 401-414. The stimulating current pulses flow substantially in the anterior-posterior direction. At this point, current can take one of two paths—either through contacting return portion 415 or through an ascending portion 421 extending upwards from base portion 425 and then through protruding return portion 440. If current runs through contacting return portion 415, it runs from base portion 425 to contacting return portion 415 (which runs substantially parallel to members of base portion 425, and is positioned directly on the skull but at a distance from members 401-414 of base portion 325) through an ascending connector 427 and back down to the level of the skull via descending portion 423. From there, current returns through lead 418 back into the power supply. If current runs through protruding return portion 440, it runs from ascending portion 421, through protruding return portion 440 (which runs substantially parallel to members of base portion 425), and back down to the level of the skull at a descending portion 423. From there, current returns through lead 418 back into the power supply. In a preferred embodiment, half of the members run through protruding return portion 440 and half of them run through contacting return portion 415. However, the invention is not limited to this proportion, and any proportion of protruding return paths and contacting return paths is possible, so long as each return path has current from at least one of the members. Current may be supplied simultaneously to all members, or alternatively, may be supplied sequentially, in a random sequence, or selectively. In another embodiment, current is supplied to member 401, and runs through a loop including each of the additional members 401-414. It should also be readily apparent that although the invention has been shown with reference to fourteen members, the invention is not in any way limited to this number, and any suitable number of members may be used. In additional embodiments, a single member may have a return path through both protruding return portion 440 and contacting return portion 415.

In the preferred embodiment depicted in FIG. 5, current from each of members 401-407 runs through contacting return portion 415 via pathways 401"-407" while current from members 408-414 runs through ascending portion 421 and through protruding return portion 440 via pathways 408"-414". Specifically, members 401-407 traverse the path A-B-C-D-E-F-G-H-A. Members 408-410 traverse the path A-I-J-K-L-M-G-H-A. Members 411-414 traverse the path A-N-L-M-G-H-A. It should be readily apparent that other combinations and pathways are possible, and are within the scope of the present invention.

Protruding return portion 414 is spaced a distance from the skull. In one embodiment, this distance is in a range of 4-10 cm. In a preferred embodiment, this distance is 7 cm. By placing the return path at a distance from the skull, electrical stimulation of unwanted portions of the brain is minimized. However, surface charge accumulation at the surface of the brain is increased. As such, some of the return paths are placed on the skull itself, so as to reduce surface charge accumulation. However, these return paths are placed a distance from the site to be stimulated within the brain so as to avoid conflicting signals in the area of stimulation. In one embodiment, the distance from the central members (such as member 414, for example) to the contacting return paths is in a range of 7-15 cm. In a preferred embodiment, the distance from the central members (such as member 414, for example) to the contacting return paths is approximately 8 or 9 cm. Thus, a balance is maintained between the need for reducing surface charge and the conflicting need to avoid electrical stimulation of unwanted portions of the brain.

In one embodiment, a screen may be applied to either of coils 300 or 400 to further reduce the magnetic field produced when electricity runs through the return portions. The screen is comprised of a material with high magnetic permeability, capable of inhibiting or diverting a magnetic field, such as mu metal, iron or steel. Alternatively the screen is comprised of a metal with high conductivity which can cause electric currents or charge accumulation that may oppose the effect produced by the return portions. Any suitable screen or shield capable of inhibiting magnetic fields may be used. The screen may be any suitable size or shape, including but not limited to sheaths of mu metal surrounding one, some or all of the members of coil 300 or 400, a flat disc of metal strategically placed, or an enclosure substantially enclosing the return paths.

Figure 6:
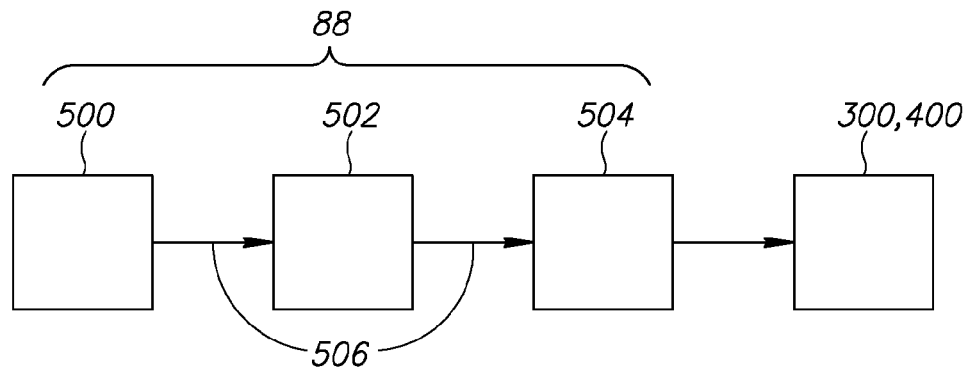
FIG. 6 is a block diagram illustration of a cooling system in accordance with a preferred embodiment of the present invention.

Reference is now made to FIG. 6, which is a block diagram illustration of a cooling system 88, in accordance with one embodiment of the present invention. Although the embodiment described herein refers to water or other liquids used for cooling, it is envisioned that air cooling may be used. The term "fluid" herein denotes liquid such as water, or gas such as a mixture of gases and more specifically, air. Cooling system 88 is designed for maintaining ambient temperature in the coils during repetitive operation. Cooling system 88 includes an external cooling unit 500, a fluid circulator 502, and an internal system 504. Internal system 504 is connected to coil 300 or 400. Arrows 506 represent the direction of cooling.

Figure 7:
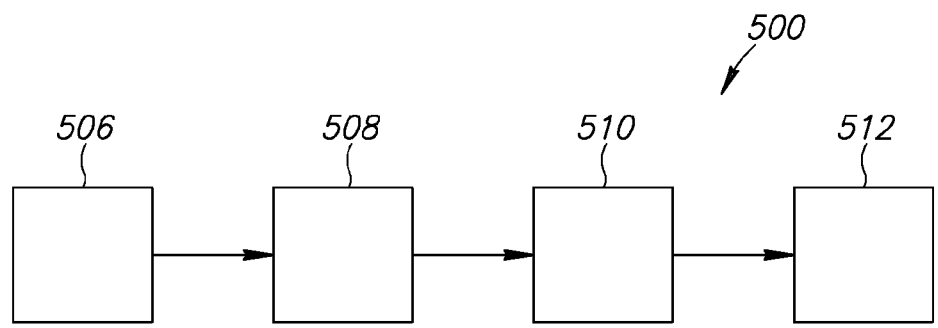
FIG. 7 is a block diagram illustration of external cooling unit from the cooling system depicted in FIG. 6.

Reference is now made to FIG. 7, which is a block diagram illustration of external cooling unit 500. External cooling unit 500 includes a compressor 506, a condenser 508, an expansion valve 510, and a carburetor 512. Compressor 506 is a commercially available compressor (available, for example, from Electrolux, Thailand, Type L57TN). In a preferred embodiment, condenser 508 is made of ⅜ inch diameter pipe, and has 0.5 horse power, a ventilator with 5-30W engine (EMI, Italy), and current of up to 0.20 A. Expansion valve 510 is made of capillary pipe having approximately a 0.07 inch diameter and a length of 4 meters. Carburetor 512 is made of a ⅜ diameter spiral pipe having a total length of at least 4.7 meters.

Figure 8:
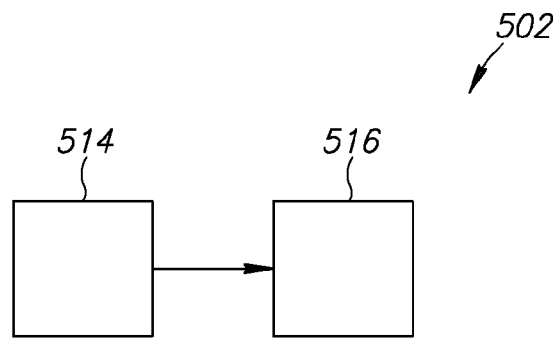
FIG. 8 is a block diagram illustration of a liquid circulator from the cooling system depicted in FIG. 6.

Reference is now made to FIG. 8, which is a block diagram illustration of fluid circulator 502. In the embodiment described herein, fluid circulator is a water circulator, and includes a water tank 514 and a water pump 516. Water tank 514 is in contact with carburetor 512 of external cooling unit 500. In a preferred embodiment, water tank 514 is a 10 liter iron tank coated by a 1 cm layer of foamed polyurethane. Water pump 516 is in fluid communication with internal system 504, and is configured to deliver cooled water to radiators of internal system 504. Water pump 516 is a commercially available water pump available, for example, from Pentax, Italy (Type CM50/01). The nominal working pressure used is 2 bar. The pressure is regulated by a manual feedback cock. The excess of water returns to the tank and creates circulation.

Cooling is accomplished as follows. Freon gas is compressed in compressor 506, condensed in condenser 508, and expanded through expansion valve 510. The capillary in expansion valve 510 is connected to carburetor 512, where the gas is evaporated again and returns to compressor 506. Carburetor 512 is immersed in water tank 514, thereby cooling the water. The water is pumped out via water pump 516, and circulated through radiators of internal system 504. In alternative embodiments, cooled air is circulated instead of water. In one embodiment, internal system 504 is a radiator system. Radiators are in thermal conjunction with coil 300 or 400, as will be described in greater detail hereinbelow with reference to FIG. 9. The fluid circulation cools the coil during pulse trains and stabilizes its temperature at mild temperature range. In one embodiment, temperature sensors are located at or near coil 300 or 400, and information about temperature during a procedure can be sent directly to cooling system 88. Automatic adjustment of cooling can then be done based on the temperature information.

Figure 9:
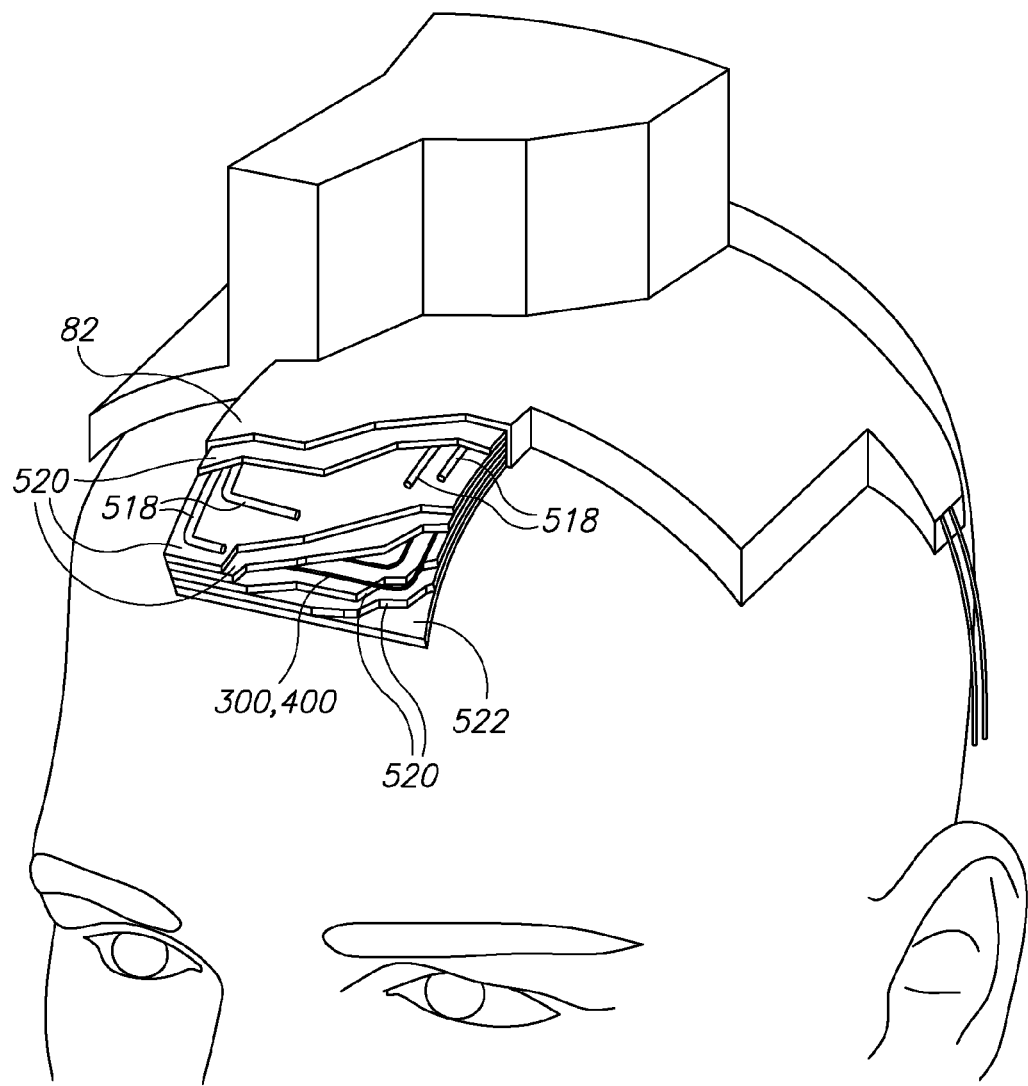
FIG. 9 is a schematic illustration of an internal system in contact with coils illustrated in FIGS. 4 and 5, in accordance with one preferred embodiment of the present invention.

Reference is now made to FIG. 9, which is a schematic illustration of internal system 504 in contact with coils 300 or 400, in accordance with one embodiment of the present invention. In the embodiment shown herein, internal system 504 includes individual radiator units 518 (shown partially cut), in close thermal contact and approximate geometric alignment with coils 300 or 400. Each of radiator units 518 are comprised of two parallel ¼ inch pipes, and between them several capillary pipes of 0.07 inch diameter. In a preferred embodiment, the pipes are made of copper and are coated by insulating lacquer (John C. Dolph Company, N.J., USA). Radiator units 518 are sandwiched by layers of a thermal and electrical insulator 520. Coil 300 or 400 is also sandwiched by layers of insulator 520. In a preferred embodiment, insulator 520 is a semi-flexible polyurethane resin, preferably Resinex 4 available from Hamchaber and Hamkasher Ltd., Bat Yam, Israel. In a preferred embodiment, at least two layers of insulator 520 are situated on either side of coil 300 or 400, and at least one layer of insulator 520 is further situated between radiator units 518 and helmet 82. An additional layer of bio compatible foam medical tape 522 (for example, Type 9776 available from 3M Center, St. Paul, Minn., USA) attaches the entire system to the head of the subject. The number of radiator units 518 depends on the number of members or coil units in the coil. For example, for coil 300, six radiator units are used, and for coil 400, seven radiator units are used.

Methods of Operation:

The basic method for operating system 80 of the present invention involves the following steps: First, subjects are fitted with earplugs to lessen any possible adverse effect on hearing. The subject is then seated on chair 85 with his/her heading resting on rear head support 87. Helmet 82 with coil 300 or 400 and radiator units 518 or with any other suitable cooling system is positioned over the subject's head over the prefrontal cortex, 5 cm anterior to the hot spot for abductor pollicis brevis (APB) muscle stimulation. The subject's motor threshold is measured by delivering single stimulations to the motor cortex, by gradually increasing the intensity (using the single pulse mode, applying one pulse each time) and recording electrical activity in abductor pollicis brevis using surface electrodes. Threshold is defined as the lowest intensity of stimulation able to produce motor evoked potentials of at least 50 µV in 5 of 10 trials. After defining the motor threshold, coil 300 or 400 is positioned on the prefrontal cortex, and the session is performed at 110% of the motor threshold. Stimulator 86 is set to required power, frequency and duration values, as determined. Frequency can range from 1-50 Hz.

Each treatment session includes a predetermined number of trains. In some embodiments, a train of 1 to 100 pulses is administered. Individual pulses measure from about 50 to 2000 microseconds, preferably in the 1000 microsecond range. In a preferred embodiment, the duration of each train is 1 second, with an inter-train interval of 20 seconds. Alternative durations and intervals are possible as well. Treatment plans can include, for example, an increase in the frequency used on different days. Pulses can vary in frequency as well as number. Certain embodiments use a frequency range of about 1 to 100 Hz.

In a preferred embodiment, each treatment session includes 42 trains. The duration of each train is 1 second and the inter-train interval is 20 seconds. Each subject undergoes three treatment sessions, on day 1, 3 and 5. On day 1, stimulation is 1 Hz, on day 2, stimulation is 10 Hz, and on day 3, stimulation is 20 Hz.

The basic principles and operation of the system is based on summation of electrical impulses. The general concept of summation is that by providing several sub-threshold impulses, it is possible to stimulate deep regions of the brain without unwanted stimulation or excessive electrical field applied at surface areas of the brain. In prior art International Publication Number WO 02/32504, this concept was applied spatially by using several coil elements carrying current in a desired direction, each placed in a different location around the head such that high electric field intensity is concentrated in a specific deep brain region, while maintaining a high ratio of deep brain electrical field to surface electrical field. This type of spatial summation can be termed one-point spatial summation, since each of the individual elements stimulates the same focused point.

While one-point spatial summation has been shown to be advantageous, other more specific methods could be useful in further increasing the depth penetration and specificity of the treatment.

In one embodiment of the present invention, a different type of spatial summation is contemplated. Rather than focusing on a single point, several points along a neuronal structure can be stimulated, causing a net result depolarization at an even lower electrical field strength. This type of spatial summation can be termed morphological line spatial summation. The points along the neuron at which the electric field is produced may or may not be in a straight line configuration. If, for example, a path of a specific axonal bundle is known, such as for example the medial forebrain bundle, the coil can be designed in a configuration to produce significant electrical fields at several points along the bundle. The configuration of the coil would approximate the path of the bundle, which can be determined, for example, by a fiber tracking diffusion tensor MRI or by other known imaging methods. This configuration may enable induction of an action potential in the bundle, while minimizing activation of other brain regions. Specifically, the coil can be activated at an intensity which is sub-threshold and thus would not induce an action potential at one specific brain region, but since it is being induced along a specific path, the summation of points in space would be enough to induce the action potential in the desired axonal bundle.

Figure 10:
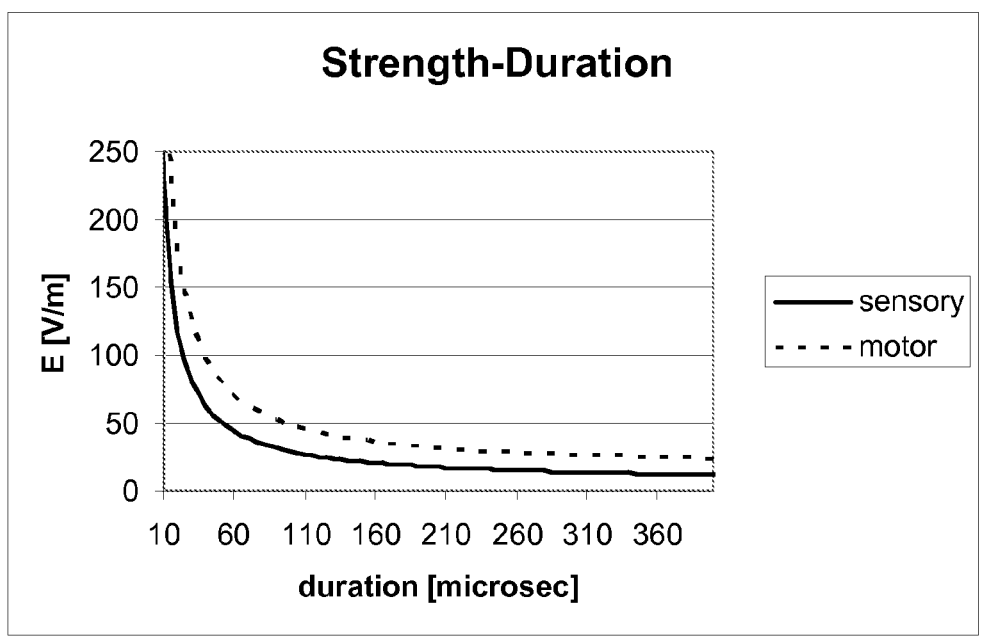
FIG. 10 is a graphical illustration of a strength/duration curve for activation of an action potential.

In another embodiment, each of the various coil members can be stimulated consecutively and not simultaneously, resulting in temporal summation. Reference is now made to FIG. 10, which is a strength/duration curve for activation of an action potential in the motor cortex and the sensory cortex, according to the data reported by Bourland et al. (Bourland J D, Nyenhuis J A, Noe W A, Schaefer J D, Foster K S, and Geddes L A, in Proc. Int. Soc. Magnetic Resonance in Medicine 4$^{th}$ Scientific Meeting, New York, 1996, p 1724). Neuronal activation threshold depends on both the strength or intensity of the electric field and the stimulation duration. In addition, the threshold may be reduced by applying several pulses with short intervals between them. Thus, it is possible to stimulate an action potential with reduced stimulation intensity by increasing the duration of the stimulation. While increasing the duration of a single pulse might be painful or detrimental to the surface areas of the brain, summing a series of individual pulses over a duration of time could have the desired effect. The coil may be designed in a configuration such that the various members are scattered around a desired region or path, and may be stimulated consecutively so that at each time period only a certain element or group of elements is activated. This way, a significant electrical field can be induced at the desired region for all time periods, or with short inter-pulse intervals that may still enable activation, while in the cortical region of the brain, only certain regions will experience a significant field at certain periods, and the intervals between experiences of significant field will be much longer. This can be accomplished by using more than one stimulator, or by using a configuration of a stimulator which includes several channels for stimulation.

A method of transcranial magnetic stimulation using temporal summation in accordance with one embodiment of the invention is as follows. A coil 300 or 400 such as the one described above with reference to FIGS. 4 and 5 is placed on the skull. In one embodiment, electrical leads are connected to one power supply or stimulator with multiple channels. In another embodiment, additional leads are separately connected to two or more power supplies and to at least two members for providing electrical stimulation. Pulses are applied at a lower voltage and/or rate of change of electric current, so that the field induced at cortical brain regions will be sub-threshold or around the threshold level, but are applied to different members at different times. In one embodiment, different stimulations are applied at 100 microsecond intervals. In other embodiments the different pulses are applied at between 10 to 1000 microsecond intervals, or even at several milliseconds intervals. In one embodiment, members are activated in a sequential order. In another embodiment, only certain members are activated, or a random pattern is generated. In other embodiments, groups of members are activated in a certain order. For example, with reference to FIG. 3A, the following sequence may be used:

Period 1: members 210-216, 234-240, 256-260
Period 2: members 218-224, 242-248
Period 3: members 226-232, 250-254

In one embodiment, two or more of the various types of summation are combined. For example, morphological line spatial summation can be used at a sub-threshold intensity in combination with temporal summation. That is, different parts of an axonal bundle can be targeted selectively or sequentially, rather than simultaneously. Alternatively, one coil can include members for one-point summation and for morphological line spatial summation. Each of the member types can be simultaneously, sequentially or selectively stimulated.

The system and methods of the present invention described herein may be used to study or treat a neurophysiological condition. A "neurophysiological condition" may be a pathological neurophysiological condition or a neurophysiological disorder, such as, but not limited to: clinical depression, non-clinical depression, dysthemia, bipolar disorder, drug addiction, substance abuse, anxiety disorder, obsessive compulsive disorder, Parkinson's disease, post-traumatic stress disorder, addictions such as smoking and alcoholism, autism, and others.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

EXAMPLE

Reference is now made to the following example, which together with the above descriptions, illustrate the invention in a non limiting fashion.

Figure 11:
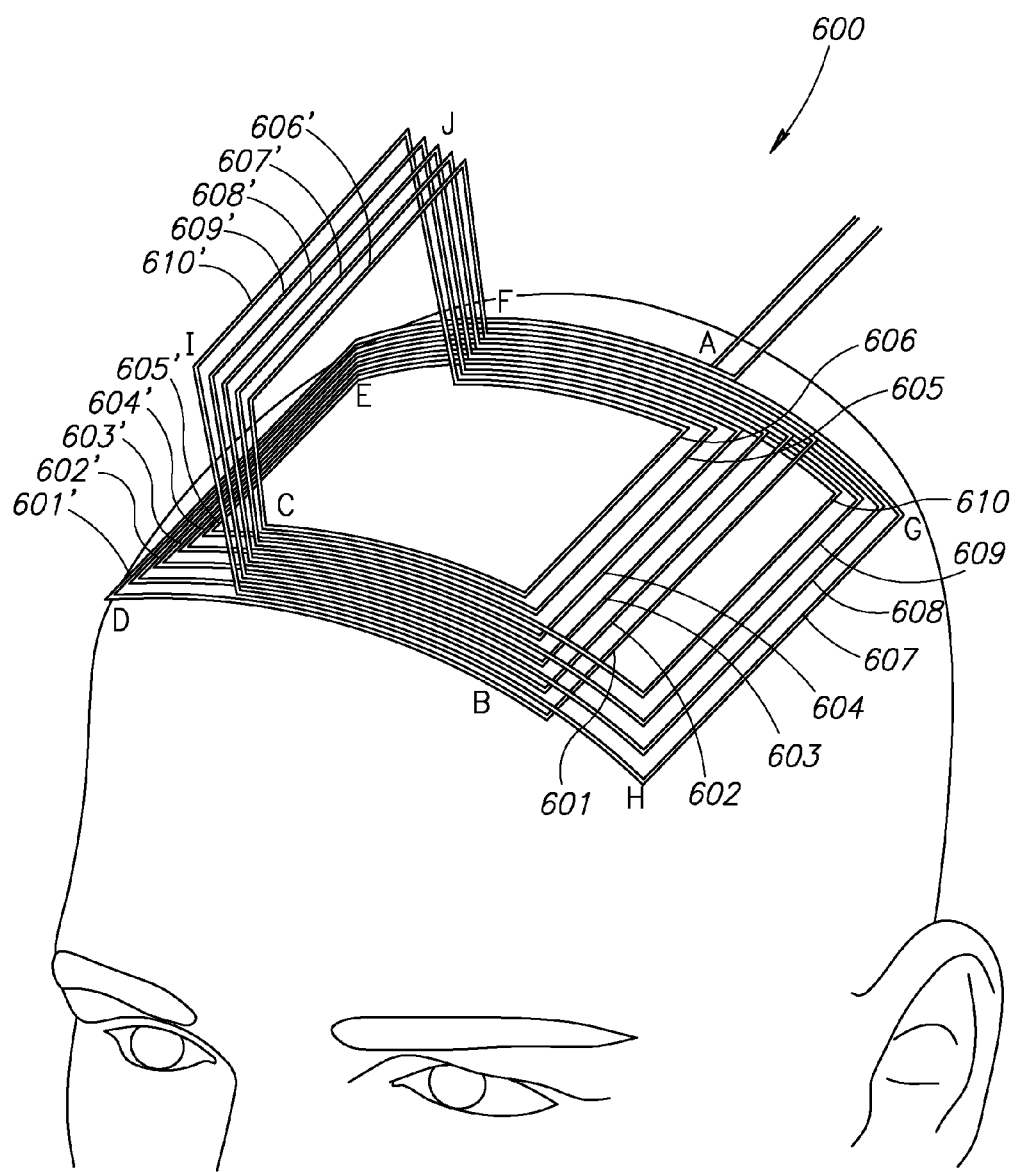
FIG. 11 is an illustration of a coil designed to stimulate the right abductor pollicis brevis in an experimental trial on humans.

The biological efficacy of a coil similar to the ones described above with reference to FIGS. 4 and 5 was tested, using motor threshold as a measure of biological effect. It should be noted that although the experimental coil, a schematic of which is shown in FIG. 11, is used to stimulate the motor cortex, a region which is accessible and measurable, the results can be appropriately compared to a coil designed to stimulate deep regions of the brain (which is more difficult to measure). This comparison was made possible by increasing the distance of the experimental coil from the site of activation (namely the motor cortex). Thus, a measure of the rate of decrease of electric field as a function of distance was taken at different distances from the skull. These measurements were compared to measurements taken under the same conditions using a standard figure-8 coil.

A coil 600 was designed to stimulate the right abductor pollicis brevis (APB), as shown in FIG. 11. The coil 600 has 10 members 601-610 split into two groups, designated by A-B and G-H in FIG. 11. The average length of the members is 11 cm. The only coil elements having radial current components are members 606-610, which are connected to the return paths shown in segments C-I and J-F. The length of the radial connecting elements is approximately 8 cm. The return paths of the other five members 601-605 are placed on the head at the contralateral hemisphere (segment D-E). The wires (segments B-C and F-A) connecting members 601-605 and return paths 606'-610' are approximately 9 cm long, on average. Coil 600 was compared to a standard commercial Magstim figure-8 coil with internal loop diameters of 7 cm.

Subjects were seated with the right forearm and hand supported. Motor evoked potentials of the right APB muscle were recorded using silver-silver chloride surface electrodes. Subjects were instructed to maintain muscle relaxation throughout the study. EMG amplitude was amplified using a conventional EMG machine (Counterpoint, Dantec Electronics, Skovlunde, Denmark) with band-pass between 10 and 2000 Hz. The signal was digitized at a frequency of 5 kHz and fed into a laboratory computer.

A Magstim Super Rapid stimulator (The Magstim Company New York, N.Y.) which produces a bi-phasic pulse, coupled with either the figure-8 coil or the H-coil, was used. Preliminary studies showed the H-coil to have a loudness level of 122 dB when activated, similar to coils 300 and 400 described above in accordance with preferred embodiments of the present invention. Subjects were fitted with foam ear plugs to attenuate the sound.

Coil 600 was placed on the scalp over the left motor cortex. The intersection of the figure-8 coil was placed tangentially to the scalp with the handle pointing backward and laterally at a 45 degree angle away from the midline. Coils were held in a stable coil holder which could be adjusted at different heights above the "hot spot" on the scalp. Resting motor threshold was determined for each coil at different distances above the scalp, at increments of 0.5 cm.

Figure 12:
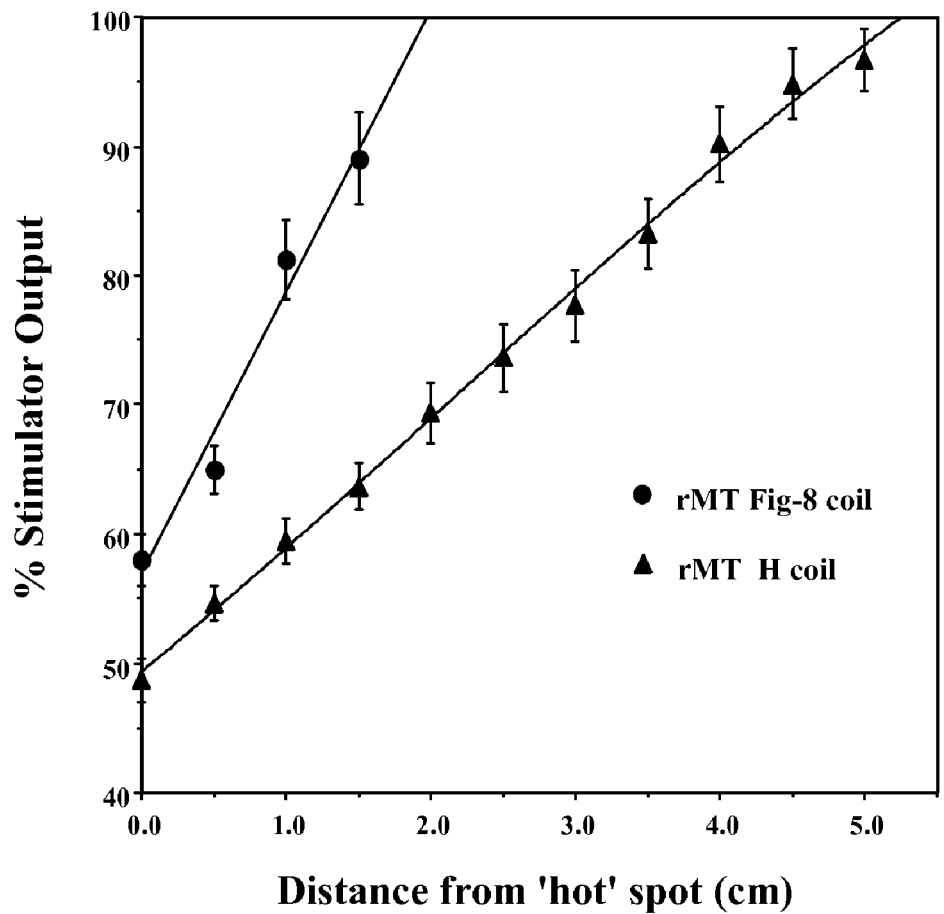
FIG. 12 is a graphical illustration of the results of performing stimulation using the coil of FIG. 11 as compared to a standard figure-8 coil.

Reference is now made to FIG. 12, which is a graphical illustration of the results of the example described above. The graph shows the percentage of stimulator output needed to reach resting motor threshold as a function of distance of the coil from the "hot spot" on the skull for both coil 600 and the standard figure-8 coil. As shown in FIG. 12, the efficacy of coil 600 at large distances from the scalp was significantly greater than for the figure-8 coil. When using maximal stimulation power output, the figure-8 coil can be effective up to 2 cm away from the coil, while coil 600 can be effective at 5.5 cm away from the coil. Moreover, the rate of decay of effectiveness as a function of the distance from the coil is much slower in coil 600 relative to the figure-8 coil.

What is claimed is:

1. A method for stimulation of a brain region, the method comprising:
   providing a first coil having a first coil base portion for delivering current to the brain region, the first coil base portion positionable on a skull; and a first coil return portion for carrying returning current, the first coil return portion at a distance from the first coil base portion;
   providing a second coil having a second coil base portion for delivering current to the brain region, the second coil base portion positionable on a skull;
   placing said first coil on the skull of a subject, such that said first coil base portion is in contact with the skull;
   placing said second coil on the skull of a subject, such that said second coil base portion is in contact with the skull;
   providing a first pulse to said first coil for activating said first coil at a level which is sub-threshold for stimulation of the brain region; and
   providing a second pulse to said second coil for activating said second coil at a level which is sub-threshold for stimulation of the brain region, wherein said providing a second pulse to said second coil is done with an interval of at least 1 microsecond and less than 1 millisecond after an end of said provided first pulse, so as to provide a summed effect in order to stimulate the brain region.

2. The method of claim 1, wherein said providing a first pulse to said first coil comprises providing multiple electrical impulses to said first coil and wherein said providing a second pulse to said second coil comprises providing multiple electrical impulses to said second coil.

3. The method of claim 1, wherein said providing a first pulse to said first coil comprises sequentially providing electrical impulses to individual members of said first coil, and wherein said providing a second pulse to said second coil comprises sequentially providing electrical impulses to individual members of said second coil, wherein said sequentially providing to said first coil is interspersed with said sequentially providing to said second coil.

4. The method of claim 1, further comprising providing a third pulse to said first or second coil, and wherein said providing a first pulse, providing a second pulse and providing a third pulse are done sequentially, randomly or selectively.

5. The method of claim 1, wherein said brain region is a deep brain region.

6. The method of claim 1, wherein said providing a first pulse comprises providing multiple pulses.

7. The method of claim 6, wherein said interval comprises multiple intervals between said multiple pulses, and wherein said multiple intervals may be varied thereby causing a particular effect on the brain.

8. The method of claim 1, wherein said interval of at least one microsecond is between 10 and 100 microseconds.

9. The method of claim 1, wherein said interval of at least one microsecond is between 1 microsecond and 100 microseconds.

10. The method of claim 1, wherein said interval of at least one microsecond is less than 10 microseconds.

11. A method of activating a neuronal structure, the method comprising:
    providing a coil for delivery of electrical impulses to a target area, the coil comprising a first individual member and a second individual member, said first and second individual members designed to carry current in predetermined directions; and
    activating said first and second individual members non-simultaneously, said activating comprising:
    providing a first pulse to said first individual member using a first source; and
    providing a second pulse to said second individual member using a second source wherein an interval between said first pulse and said second pulse is at least 1 microsecond and less than 1 millisecond.

12. The method of claim 11, wherein said coil is designed to carry current in predetermined directions, wherein said predetermined directions form a path designed to mimic a neuronal structure.

13. The method of claim 11, further comprising providing a third pulse to said coil, and wherein said providing a first pulse, providing a second pulse and providing a third pulse are done sequentially, randomly or selectively.

14. The method of claim 11, wherein said interval is between 10 and 100 microseconds.

15. The method of claim 11, wherein an interval between said first pulse and said second pulse is between 1 microsecond and 100 microseconds.

16. The method of claim 11, wherein an interval between said first pulse and said second pulse is less than 10 microseconds.

17. The method of claim 11, wherein said predetermined directions are a same direction for each of said first and second individual members.

18. The method of claim 11, wherein said predetermined directions are a different direction for each of said first and second individual members, and wherein each of said predetermined directions forms a path designed to mimic a neuronal structure.

19. The method of claim 11, further comprising a third individual member, and wherein said activating further comprises activating said first, second and third individual members non-simultaneously, said activating further comprising providing a third pulse to said third individual member, using either said first or second source or a third source.

20. The method of claim 19, wherein said activating comprises activating each of said first, second and third individual members in at least one of the following ways: sequentially, randomly, and selectively.

21. The method of claim 11, wherein said activating is done at a sub-threshold level for at least one of said first and second individual members, and wherein said activating said first and second individual members non-simultaneously provides a summed effect in order to stimulate a deep brain region.

22. The method of claim 11, wherein said providing a coil comprises providing multiple coils, and wherein said activating said first and second individual members comprises activating a first individual member of a first coil of said multiple coils and a second individual member of a second coil of said multiple coils.

23. The method of claim 11, wherein said providing a first pulse comprises providing multiple pulses.

24. The method of claim 23, wherein said interval comprises multiple intervals between said multiple pulses, and wherein said multiple intervals may be varied thereby causing a particular effect on the brain.

* * * * *